United States Patent
Zeman

(10) Patent No.: US 6,170,337 B1
(45) Date of Patent: Jan. 9, 2001

(54) METHOD AND DEVICE FOR MEASURING PERMANENT LENGTH DEFORMATIONS OF MATERIALS

(76) Inventor: Jindřich Zeman, Na Břevnovské pláni 31/2223, 169 00 Praha 6 (CZ)

( * ) Notice: Under 35 U.S.C. 154(b), the term of this patent shall be extended for 0 days.

(21) Appl. No.: 09/349,582

(22) Filed: Jul. 8, 1999

(30) Foreign Application Priority Data

May 28, 1999 (CZ) .............................................. PV 1899-99

(51) Int. Cl.[7] .................................................. G01N 19/06
(52) U.S. Cl. .................................. 73/783; 73/806; 73/762
(58) Field of Search .......................... 73/762, 774, 786, 73/800, 806, 856, 783

(56) References Cited

U.S. PATENT DOCUMENTS

| | | | | |
|---|---|---|---|---|
| 3,594,912 | * | 7/1971 | Sauterel | 33/523 |
| 4,031,746 | * | 6/1977 | Furuta et al. | 73/800 |
| 4,483,075 | * | 11/1984 | Kundin | 331/21 |
| 4,669,106 | * | 5/1987 | Ammerman | 378/208 |
| 5,668,324 | * | 9/1997 | Voss et al. | 73/800 |

* cited by examiner

*Primary Examiner*—Max Noori
(74) *Attorney, Agent, or Firm*—Notaro & Michalos P.C.

(57) ABSTRACT

A method for measuring permanent length deformations in materials includes determining a change of an initial distance between two measuring points on the material surface. A first pair of impressions is formed on a portable impression body that corresponds to these two measuring points prior to the expected deformation and a second pair of impressions is formed after a critical loading of the material. The distances between the first and the second pairs of impressions are then compared. A device for carrying out the method uses a fixed portion arranged on the material being measured and a portable impression body. The fixed portion of the device is provided with a pair of measuring elements which correspond to the measuring points disposed at a mutual distance from each other, and the portable impression body of the device has an impression face adapted for receiving the impressions that are created by the measuring elements.

9 Claims, 1 Drawing Sheet

METHOD AND DEVICE FOR MEASURING PERMANENT LENGTH DEFORMATIONS OF MATERIALS

FIELD OF THE INVENTION

The invention relates to a method for measuring permanent length deformations of materials, comprising a step of determining a change of the initial distance between two points on the material surface. The invention relates also to a device for carrying out said method, comprising two measuring elements fastened in a mutual distance on the material surface.

DESCRIPTION OF THE PRIOR ART

Measuring of length deformations in solid substances, particularly in metallic and other materials which are, when mechanically stressed, deformed and strained beyond the limit of elasticity and the yield point in tension with increasing deformation up to the final fracture, has been carried out using mechanical or optical extensometers measuring the material stretch between two fixed points on a structure. Said extensometers require, due to their limited accuracy, a larger distance, e.g. about several tens of centimeters, between said two fixed points on the material or the structure. In order to attain greater accuracy when measuring the distance of the reference points from each other, thus enabling the distance between them to be shorter, it can be possible to use measuring microscopes. The basic disadvantage of these apparatuses consists in their large dimensions and thus their considerable weight, which makes these apparatuses not applicable in practice for measuring deformations on erected metallic structures, e.g. bridges, pipings etc., particularly when these pipes are positioned in narrow spaces, e.g. in atomic power plants. A further considerable problem consists in difficult accessibility of the measuring points e.g. on insulated oil pipeline, distributing pipes inside structures, on bridges etc.

It is therefore the object of the invention to provide a method and a device for measuring permanent length deformations of solid substances and materials of structures, which deformations are caused by excessive or long-term loading of the structure, wherein said method should be carried out in conditions enabling to attain the highest possible measuring accuracy, e.g. in laboratories or in equipped measuring stations being situated at a distance from the measured structure.

SUMMARY OF THE INVENTION

In one aspect of the invention said method for measuring permanent length deformations of materials, comprising the step of determining a change of the initial distance between two points on the material surface, is characterized by making impressions of the measuring points which had been formed on the material surface, on a removable impression body and by measuring the exact distance of the identifiable positions of both measuring points on the impressions of said measuring points.

In another aspect of the invention, a first pair of the measuring point impressions is made on said removable impression body prior to the deformation of the material and a second pair of the measuring point impressions is made after the critical loading of the material, and the distances of the first pair of the impressions and of the second pair of the impressions are compared and evaluated.

The device for carrying out said method consists of a fixed portion arranged on the material section being measured and of a portable portion, the fixed portion of the device being provided with two measuring elements having identifiable measuring points disposed at a mutual distance, and the portable portion comprising an impression body with an impression face adapted for making the impressions of the measuring points.

In still another aspect of the invention, the measuring elements are fastened on a common plate which itself is fastened on the surface of the material section being measured. Said measuring elements are formed by the top part of a pyramidal body having always at least one of its side sharp edges parallel with at least one of the side edges of the other pyramidal body of the second measuring element. The fastened plate is preferably surrounded by a guide ring having inner guiding surface for the impression body, said guide ring being fastened to the material section being measured.

The method and the device according to the invention provide a possibility for exact measuring of permanent (nonreversible) deformations of material on short length sections by using very accurate measuring devices, e.g. measuring microscopes. Since this bulky and heavy apparatus is not suitable to be used directly in the terrain, e.g. on a bridge, an oil pipeline, a ship or other structure, where measuring the state of the structure is necessary, e.g. after an earthquake or other excessive loading, it is advantageous to use the device according to the invention which supposes measuring the distance between the measuring elements prior to and after the loading by measuring said distance of the impressions of the measuring points formed on the removable impression body using a measuring microscope.

BRIEF DESCRIPTION OF THE DRAWINGS

An example embodiment of the invention is illustrated on the accompanying drawings, in which.

DETAILED DESCRIPTION OF THE PREFERRED EMBODIMENT

Figure 1:
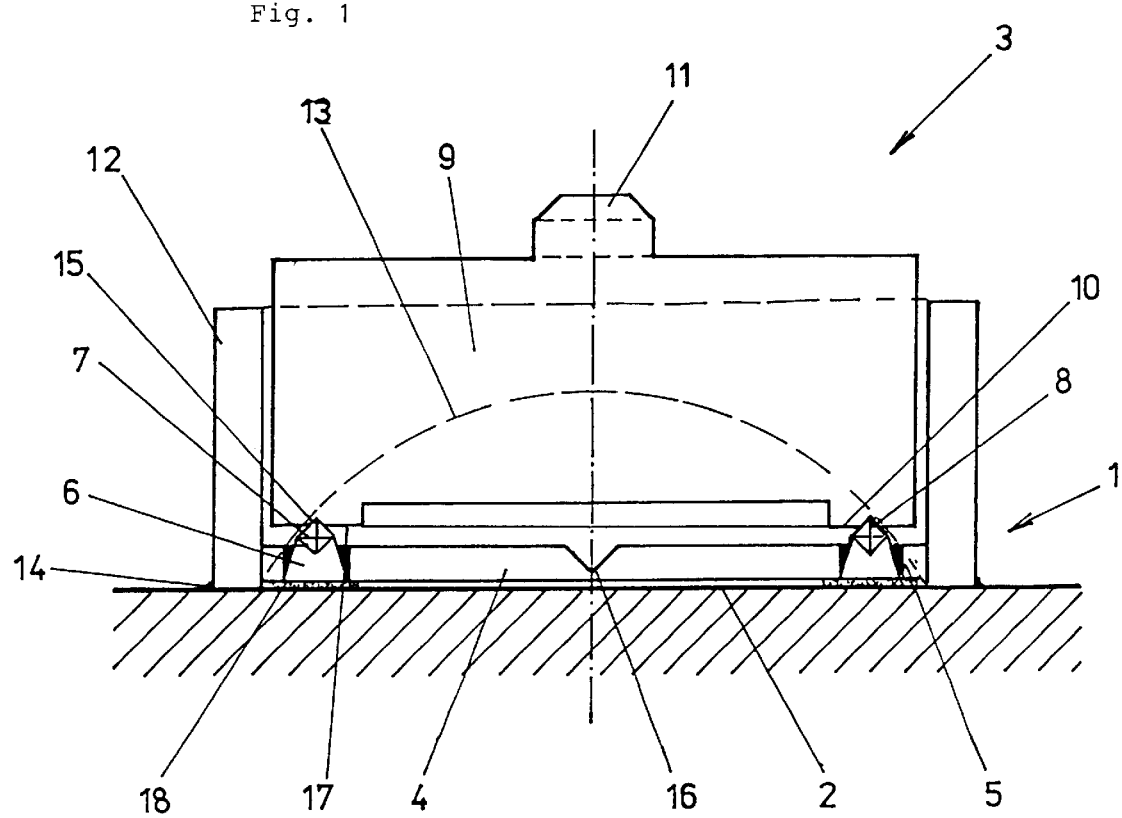
FIG. 1 is a longitudinal section of the part of the material being measured on which the fixed portion of the device being provided with two measuring elements (points) is fastened, whereas portable portion of the device is disposed above said fixed portion and is ready to be transported to a measuring station, said section being taken along the plane A—A of FIG. 2.
Figure 2:
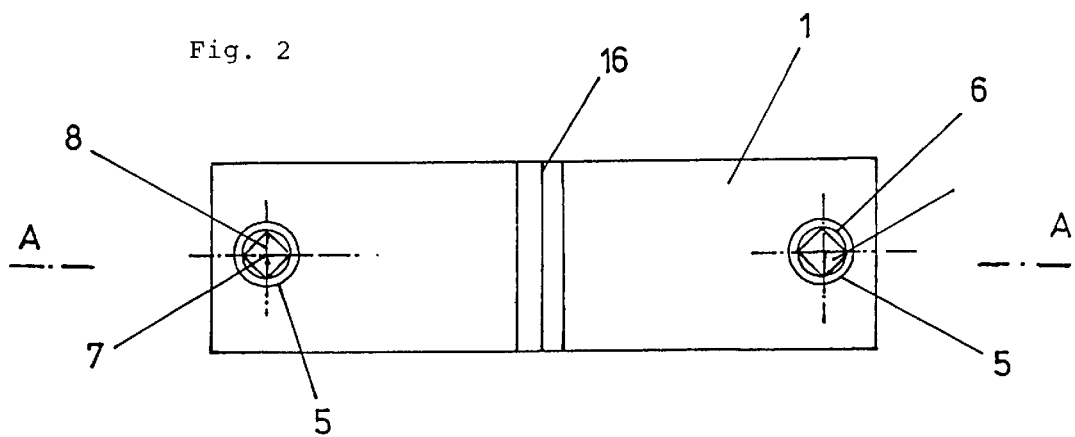
FIG. 2 is a top view of said plate with the measuring elements.

A device for measuring permanent (non-elastic) length material deformations in solid substances, in this example in metallic materials, consists of a fixed portion 1 of the device which is fastened onto the material section 2 being measured, and of a portable portion 3 of the device formed by an impression element capable of being transported off the measuring place.

Said fixed portion 1 of the device is formed by a plate 4 having, in the embodiment depicted in the drawings, the form of a rectangular plate and being provided with two holes 5 in two places in end areas of its surface, which holes 5 are, in the embodiment depicted, through-holes reaching to the lower surface of the plate 4; said holes 5 may also be formed as blind holes. In each of said holes 5 a holder 6 in the form of an anchoring body having a truncated pyramidal or conical shape is fastened, e.g. by embedding in a casting material 17 filing the holes 5, wherein the larger base of the holder 6 is plane and perpendicular to the normal line drawn to the surface of the material section 2 being measured; this surface may be plane, e.g. on bridge structures, cylindrical with a relatively large radius of curvature, e.g. on oil pipelines or other pipes with larger diameter, or otherwise curved on the hull of tanker ships and other structures with variable shapes. The upper pyramidal parts of the measuring elements 7, tapering into measuring points having the form of tips or edges, projects upwards from the smaller bases of both holders 6.

In the embodiment depicted, said measuring point of the measuring element 7 is formed by a top part of a tetrahedral diamond pyramid which is usually used for Wickers hardness measuring of solid substances, wherein at least one side sharp edge 8 of said pyramid ending in the top point of the measuring element 7 is perpendicular to the connecting line of the tops of said two tetrahedral diamond pyramids so that both the measuring tips extend into the side sharp edge 8 which is parallel with the side sharp edge 8 of the other measuring tip. The exact parallel positions of said side sharp edges 8 are important for enabling exact measuring which will be described in the next part of the description.

The measuring plate 4 with measuring elements 7 is fastened permanently on the measured section 2 of a bridge structure, an oil pipeline, ship hull or similar structure by means of glue which is capable to follow the extensions and deformations of the material in the measured section 2 without failure and which is applied on the lower surface of the plate 4 in the form of two adhesive discs 18 formed on the lower surface of the holder 6 and the lower surface of the plate 4 around said holes 5 or; in the case of a blind hole, said glue is applicated on the lower surface against the bottom of said blind hole. In order not to affect the deformations of the material section 2 being measured, the plate 4 is, in its central portion, provided with a weakening 16 of its cross section which is, in the embodiment depicted, formed by a groove having a triangular cross section, but in other cases said weakening 16 may be formed by e.g. a row of holes etc.

The second portion of the device is represented by said portable portion 3 being formed by an impression body 9 having the shape of a roller with an impression face 10 which is perpendicular to a longitudinal axis of the cylindrical impression body 9 made of a soft metal, e.g. of lead, or a waxy material, e.g. a dental wax, etc. The impression body 9 is, in the embodiment depicted, made of a soft metal and is provided on a face opposite to the impression face 10 with an axial impact projection 11. For better guiding of the impression body 9 during making impressions of the measuring elements 7, the device according to this example is provided with a guide ring 12, the circumferential walls thereof being preferably bevelled on two opposite sides by inclined cutting planes so that the guide ring 12 has rounded cut-outs 13 on its two opposite sides, whose shape is recognisable from FIG. 1, and which enable to check the state of the plate 4 with the measuring tips. The guide ring 12, in addition to the function of guiding the impression body 9, also has protective function and protects the fixed portion 1 of the device against damage, wherein said guide ring 12 serves also for easier finding relatively small plates 4 on larger structures, e.g. on the oil pipelines or on the ship hulls. The guide ring 12 is fastened to the surface of the material section 2 being measured outside of the areas of the rounded cut-outs 13 by means of e.g. spot welds 14.

The measuring of permanent length deformations in materials, particularly after extreme loading, e.g. after earthquakes, landslipes or long-time or repeatedly acting loadings, is carried out, according to the method of the invention, using the described device, by an indirect method when it is not the distance between said two measuring elements 7 on the plate 4 glued fixedly and permanently on the observed material that is directly measured, but the distance between impressions 15 of these measuring tips on the measuring elements 7, which impressions were made either by pushing the impression face 10 of a wax impression body 9 against the pair of the measuring elements 7, or by impinging the impression face 10 of the impression body 9 made of a soft metal, e.g. lead, by means of hammer blows, or another tool blows, directed on the axial impact projection 11 ensuring axial and consequently uniform acting of blows on said pair of the measuring elements 7.

When each of the measuring elements 7 is a diamond employed usually e.g. for Wickers hardness measuring, whose upper part protruding upwards from the holder 6 has the shape of a tetrahedral pyramid having two sharp edges 8 on the both measuring elements 7 exactly parallel to each other, then the impressions 15 formed in the impression face 10 of the cylindrical impression body 9 have the shape of pyramidal dents with sharp edges intersecting at one point in the deepest place of the cents, wherein at least two of these edges of the both impressions 15 are mutually exactly parallel.

After making said impressions 15 of the top areas of the measuring elements 7 of the fixed portion 1 of the device according to the invention, the fixed portion 1 being fastened on the measured structure, said portable part 3 of the device represented by the impression body 9 is, according to the method of the invention, removed from the guide ring 12 and transferred to a measuring laboratory, a measuring station etc. provided with an exact measuring apparatus, e.g. measuring microscope (not shown on the drawings), by means of which the distance between the parallel edges of the impressions 15 made by the measuring elements 7 can be measured with high accuracy.

The essence of said indirect method for measuring permanent deformations of material on various structures resides in that during the period of putting said structure into service, a set of the plates 4 with measuring elements 7 is glued at various places of the surface and, after this permanent fastening of the measuring elements 7, a pair of basic impressions 15 on the portable portion 3 of the device, i.e. on the impression body 9, is made. Said impression body 9 is then removed, provided with identification mark of a concrete plate 4 and optionally with data describing the thermal conditions at the time of making the impression 15 and the distance between the identifiable measuring points of said impressions 15 is measured, and the so obtained length data are stored for further use.

When critical strains of the structure have occured, e.g. after earthquake, or after long-term loading of the structure of e.g. a tanker ship etc., when it is necessary to find out whether the strained material has not been deformed beyond the limit of elasticity and whether $\Delta l$ in the tensile diagram $\sigma$ ($kg/mm^2$)–$\Delta l$ (mm) has increased beyond the yield point, when it would be necessary to repair or destroy the structure, then the stored length data or the respective impression body 9 is found and the impression body 9 is transferred to the corresponding plate 4 with the measuring elements 7 and said measuring elements 7 are then impressed again into the impression face 10 of the same or another impression body 9. Said impression body 9 may then be transferred again into the laboratory for measuring the precise actual distance of the measuring points on the both new impressions 15, e.g. by means of a measuring microscope, the comparison of both length values indicating the state of the structure at the time of the second measuring.

Said measuring device is useful especially for watching the static loading capacity of e.g. bridge structures after an excessive loading, e.g. by an earthquake, since the beams of the bridge structure may be provided already during the construction or later on in the course of the ussual service of the structure by a sufficient number of the measuring plates 4 and after fastening thereof it is possible to make the impressions 15 on the same number of the impression bodies 9 as a basis for exact measuring. The measuring device may be employed especially also on oil pipelines embedded on an unstable subsoil or on a subsoil dammaged e.g. by earthquake, on ship hulls of big tankers and other ships, on piping systems in atomic power stations, for deformation measuring on airplane, rocket, space shuttle structures etc.

What is claimed is:

1. A method for measuring permanent length deformations of a material having a material surface, comprising:

providing on the material surface, first and second spaced apart measuring elements (7) which are each capable of making an impression (15) in a removable impression body (9);

pressing said removable impression body (9) against the first and second measuring elements (7) to form a pair of spaced apart impressions (15) in the removable impression body; and measuring an exact difference between the impressions on the removable impression body for establishing a measurement for a distance between the measuring elements.

2. A method according to claim 1 wherein said impressions in the removable impression body are made before a deformation of the material between the measuring elements has occurred, the method further including, after the material has been deformed between the measuring elements and beyond a critical load, pressing a removable impression body (9) again against the measuring elements for forming a second pair of impressions, measuring the distance between the second pair of impressions, and comparing the distance between the first mentioned pair of impressions and the second pair of impressions to provide a measurement of the deformation.

3. A device for measuring permanent length deformation of a material having a material surface by measuring a distance between impressions in a removable impression body, comprising:

a fixed portion (1) connected to the material along the material surface;

a pair of spaced apart measuring elements (7) each fastened to the material surface and spaced apart by a distance to be measured, the measuring elements being provided with the fixed portion (1) on the material surface; and a portable portion (3) including an impression body (9) with an impression face (10) adapted to be pressed against the measuring elements for making a first pair of impressions (15) in the impression face, a distance between the first pair of impressions being used as a measurement of a distance between the measuring elements on the material surface.

4. A device according to claim 3 wherein the fixed portion includes a plate (4) fastened to the material surface.

5. A device according to claim 3 wherein each of said measuring elements comprises a top pyramid body, each pyramid body having a sharp edge (8), the sharp edges of the pyramid bodies being parallel to each other.

6. A device according to claim 5 wherein the sharp edges of the pyramid bodies are perpendicular to a line connecting the measuring elements to each other.

7. A device according to claim 3 including a guide ring (12) around the pair of measuring elements for guiding movement of the impression body against the measuring elements.

8. A device according to claim 7 wherein the fixed portion includes a plate (4) fastened to the material surface.

9. A device according to claim 8 including a pair of spaced apart bores in the plate each for receiving one of the measuring elements.

\* \* \* \* \*